United States Patent
Sacherer

(10) Patent No.: US 8,663,558 B2
(45) Date of Patent: Mar. 4, 2014

(54) DEVICE FOR ANALYZING A BODY FLUID

(75) Inventor: Klaus-Dieter Sacherer, Kirchheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1350 days.

(21) Appl. No.: 11/447,783

(22) Filed: Jun. 6, 2006

(65) Prior Publication Data
US 2007/0065340 A1 Mar. 22, 2007

(30) Foreign Application Priority Data
Jun. 14, 2005 (EP) .................................... 05012701

(51) Int. Cl.
*B65D 83/08* (2006.01)

(52) U.S. Cl.
USPC ........... 422/68.1; 422/500; 422/554; 422/560

(58) Field of Classification Search
USPC ......................... 422/66, 68.1, 500, 554, 560
See application file for complete search history.

(56) References Cited

U.S. PATENT DOCUMENTS

| | | | |
|---|---|---|---|
| 5,077,010 A | 12/1991 | Ishizaka et al. | |
| 5,660,636 A * | 8/1997 | Shangold et al. | 118/500 |
| 6,534,017 B1 | 3/2003 | Bottwein et al. | |
| 7,378,270 B2 * | 5/2008 | Azarnia et al. | 435/287.2 |
| 2003/0079444 A1 * | 5/2003 | Behnke | 53/467 |
| 2005/0230253 A1 | 10/2005 | Marquant | |
| 2005/0245954 A1 * | 11/2005 | Roe et al. | 606/181 |
| 2005/0281706 A1 * | 12/2005 | Funke et al. | 422/63 |

FOREIGN PATENT DOCUMENTS

WO   WO 2004/056269 A1   7/2004

\* cited by examiner

*Primary Examiner* — Paul Hyun
(74) *Attorney, Agent, or Firm* — Woodard, Emhardt, Moriarty, McNett & Henry LLP

(57) ABSTRACT

The invention concerns a device for analyzing a body fluid. The device includes a test tape having a carrier tape and test fields for the detection of an analyte in the body fluid, the test fields being distributed along the carrier tape and raised above the carrier tape and a container for the test tape. The container has a seal for passage of the test tape, wherein the test fields have a leading edge which runs against a sealing edge of the seal when the test field passes through the seal. The leading edge of the test fields or/and the sealing edge of the seal at least in parts are angled or curved relative to the transverse direction of the tape.

21 Claims, 2 Drawing Sheets

US 8,663,558 B2

DEVICE FOR ANALYZING A BODY FLUID

REFERENCE TO RELATED APPLICATIONS

This application claims priority to EP 05012701.8 filed Jun. 14, 2005.

TECHNICAL FIELD

The invention concerns a device for analyzing a body fluid in particular for blood sugar tests.

BACKGROUND

Test tapes with a plurality of test fields for the detection of an analyte in body fluid can be used as consumable cassettes especially for determining blood sugar in automated hand-held devices that can also be used by laymen to carry out the required analytical steps in a simple and rapid manner. A plurality of test fields provided with a suitable test chemistry are arranged consecutively on the wound test tape instead of conventional individual test strips. The body fluid is applied to a test field that is moved into an active position by advancing the tape in order to then be able to carry out a test, an example of which is by means of an optical analysis. In this manner it is possible to carry out numerous tests without having to separately handle and dispose of disposable test strips.

In WO 2004/056269 A1, various sealing concepts are described for protecting the unused part of the test tape in a container against damaging environmental influences while at the same time allowing tape transport for the successive provision of the test fields. Seals are also disclosed with sealing lips which extend parallel to the front edge of the test fields.

SUMMARY OF THE INVENTION

On this basis, an embodiment of the present invention provides a device such that the tape movement is further optimized with regard to the requirements for the drive.

In accordance with an embodiment of the invention, a device for analyzing a body fluid is provided. The device comprises a test tape having a carrier tape and test fields for the detection of an analyte in the body fluid, the test fields being distributed along the carrier tape and raised above the carrier tape and a container for the test tape. The container has a seal for passage of the test tape. The test fields have a leading edge which runs against a sealing edge of the seal when the test tape passes through the seal. The leading edge of the test fields at least in parts are angled relative to a transverse direction of the tape.

In accordance with an embodiment of the invention, a device for analyzing a body fluid is provided. The device comprises a test tape having a carrier tape and test fields for the detection of an analyte in the body fluid, the test fields being distributed along the carrier tape and raised above the carrier tape and a container for the test tape. The container has a seal for passage of the test tape. The test fields have a leading edge which runs against a sealing edge of the seal when the test field passes through the seal. The sealing edge at least in parts are angled or curved relative to a transverse direction of the tape.

In accordance with an embodiment of the invention, a device for analyzing a body fluid is provided. The device comprises a test tape having a carrier tape and test fields formed for the detection of an analyte in the body fluid that are distributed along the carrier tape and are raised above the carrier tape and a container for the test tape. The container has a seal for passage of the test tape. The test fields have a leading edge which runs against a sealing edge of the seal when the test tape is pulled through the seal. The leading edge of the test fields passes the sealing edge in sections during passage through the seal.

BRIEF DESCRIPTION OF THE DRAWINGS

The invention is elucidated in more detail in the following by the embodiments shown schematically in the drawing.

DETAILED DESCRIPTION OF THE DRAWINGS

The idea behind the invention is to adapt the geometry of the test fields and the seal to one another such that the tape passage is facilitated. As such, it is proposed according to the invention that the leading edge of the test fields facing in the direction of tape transport or/and the effective sealing edge for the test fields is/are angled or bent relative to the transverse direction of the carrier tape. As a result the leading edge and sealing edge enclose an angle that is different from zero thus avoiding an abrupt edge contact over a large width which lowers or flattens the peak force when the respective test field is pulled through the seal.

In order that the force increases gradually over the tape width, an embodiment of the invention provides that test fields have a tip delimited by the leading edge that points towards the sealing edge.

The leading edge of the test fields, in an embodiment of the invention, extends diagonally to the longitudinal direction of the tape at an angle that differs from 90° over the width of the test fields. Further, an embodiment provides that the sealing edge interacting with the test tape is diagonal to the longitudinal direction of the tape over their tape width.

To avoid the occurrence of peak forces, the sealing edge and the leading edge should enclose an angle of at least 5° in an embodiment of the present invention.

Another embodiment provides that the seal is profiled for a gentle tape entry and is in specific embodiments is rounded in the vertical direction of the test tape.

The sealing concept according to an embodiment of the invention is used for a container that is formed by a cassette where the seal seals the outlet area of a storage chamber of the test tape cassette.

For a good sealing action, the seal has a flexible sealing area that can be pressed against the broad side of the carrier tape that carries the test fields.

In an embodiment of the invention, for manufacturing, the test fields are applied to the test tape as prefabricated flat material components and in specific embodiments are glued onto the test tape.

One embodiment of the invention is also that the leading edge of the test fields passes the sealing edge in sections during passage through the seal.

Figure 1:
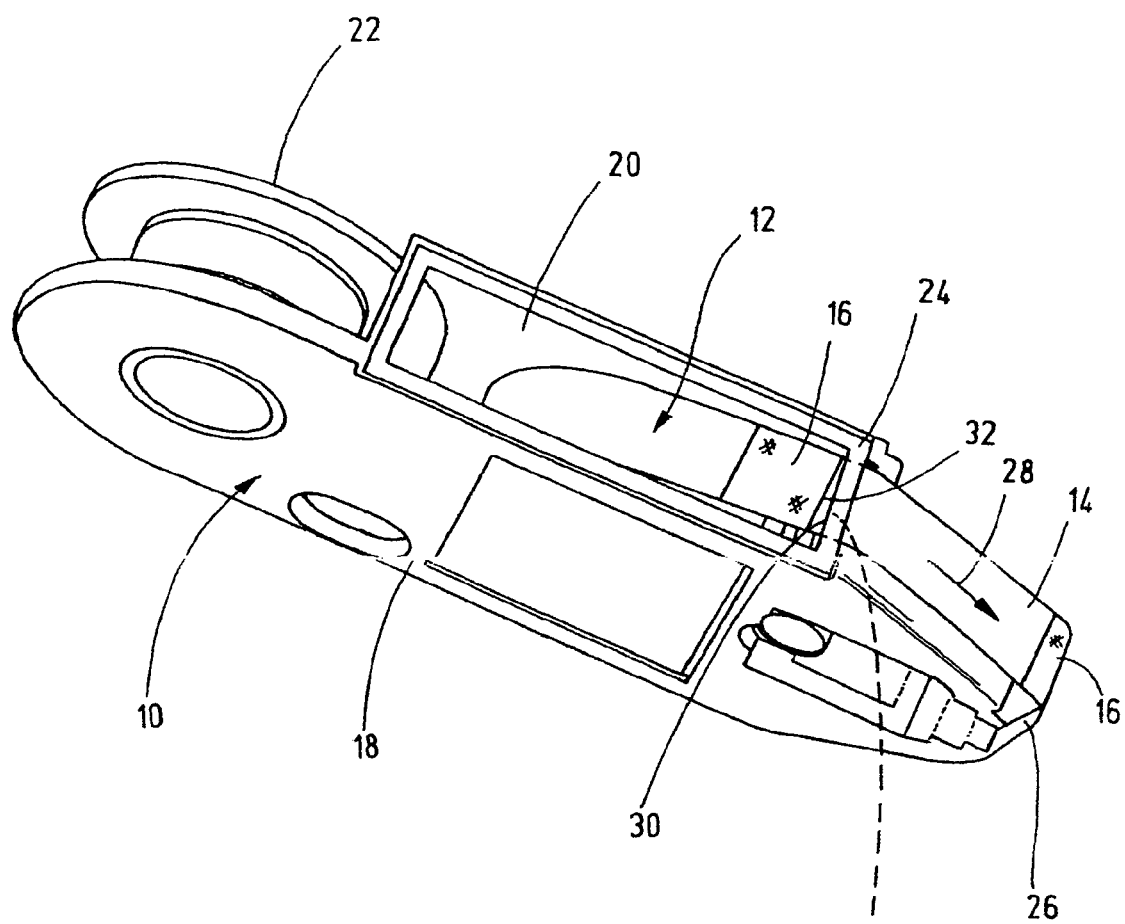
FIG. 1 shows test tape cassette for blood sugar tests with a sealed tape passage in a perspective, partially broken open view.

The test tape cassette 10 shown in FIG. 1 contains a test tape 12 which comprises a carrier tape 14 and a plurality of test fields 16 applied to the carrier tape spaced apart from one another in the longitudinal direction of the tape for detection of an analyte, a non-limiting example of which is blood sugar in a blood sample. The cassette 10 has a container or holding housing 18 with a storage space 20 for unused test tape which is expediently in the form of a tape coil and with a drawing spool 22 for used test tape. A seal 24 statically seals the storage space 20 from the outside against a cover that is not shown whereas a sealing slit allows the test tape 12 to be pulled through so that sample liquid or blood can be applied to unused test fields 16 at a deflection head 26.

The test fields 16 are applied to the test tape as prefabricated flat material components. In a non-limiting example, the test fields are glued onto the carrier tape 14 as prefabricated, label-like, cut-to-size parts and are consequently raised above the carrier tape. The test fields 16 thus have a leading edge 32 which runs against a sealing edge 30 of the seal 24 in the tape pulling direction (arrow 28). As such, the leading edge 30 of the test fields 24 at least in parts are angled relative to a transverse direction of the tape 14. It is appreciated that a transverse direction is a direction generally perpendicular to the direction of working, in this case, the tape pulling direction (arrow 28).

In the embodiment shown in FIG. 1 the leading edge 32 of the test fields 16 extends over the width of the carrier tape 14 orthogonally to the longitudinal direction of the tape whereas the sealing edge 30 on the inlet side extends obliquely thereto at an acute angle thus enabling the tape to be pulled through gently. For this purpose the angle enclosed by the sealing edge 30 and the leading edge 32 should be at least 5°.

The sealing edge 30 of the seal 24 is expediently additionally profiled for a gentle tape entry and is in particular rounded towards the top away from the broad side of the tape 12. The effective sealing edge 30 is in this case defined by the sealing line that engages with the carrier tape 14 or the test field structure 16. In contrast to a contact-free slit seal, the seal 24 has a flexible sealing area 34 for a dragging surface seal that can be pressed against the carrier tape 14.

Figure 2:
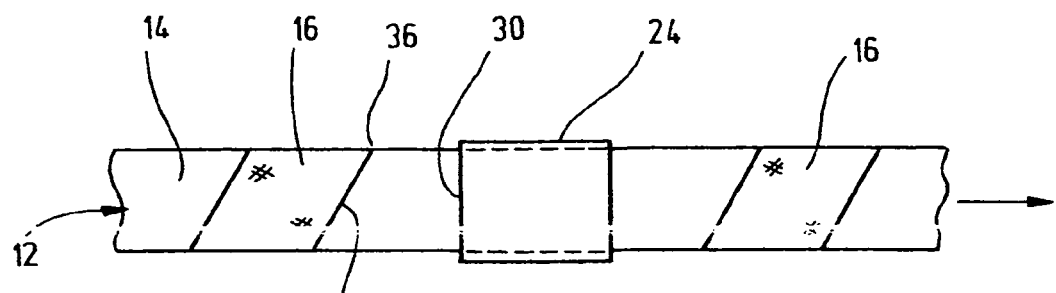
FIG. 2 shows a test tape with obliquely positioned test fields in a partial top-view.

In the embodiment shown in FIG. 2 the occurrence of peak forces when the tape is pulled through the seal 24 is avoided by positioning the test fields 16 at a slanted angle on the carrier tape 14. The leading edge 32 thus extends diagonally to the longitudinal edge of the tape at an angle that is different from 90°. In this manner the test fields 16 have a tip 36 pointed towards the sealing edge 30 of the seal 24 that extends orthogonally to the longitudinal direction of the tape, said tip 36 firstly passing the sealing edge 30 such that the tape drive force only has to be gradual in order to overcome the resistance to passage.

Figure 3:
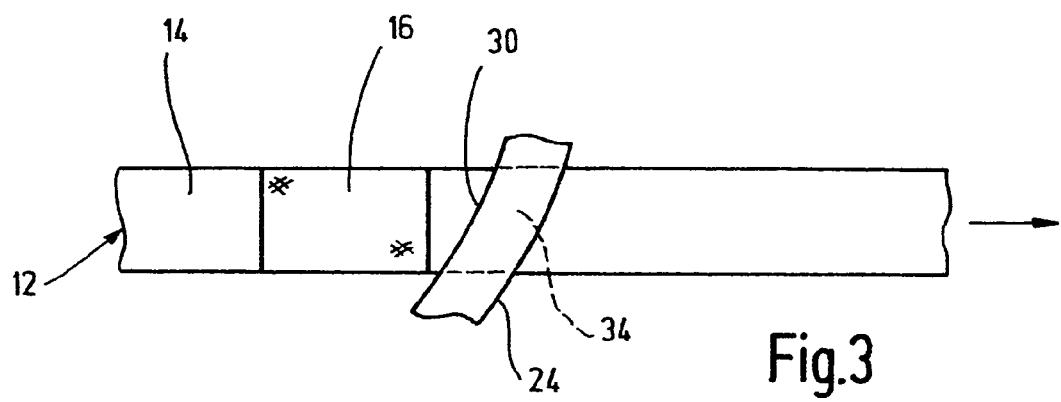
FIG. 3 shows another embodiment in a view corresponding to FIG. 2.

In the embodiment according to FIG. 3 rectangular test fields 16 as in FIG. 1 are applied to the carrier tape 14 whereas the sealing edge 30 of the seal 24 extends in a curved manner transversely to the tape direction. This measure also ensures a gentle entry of the raised test fields 16 into the sealing area 34.

Figure 4:
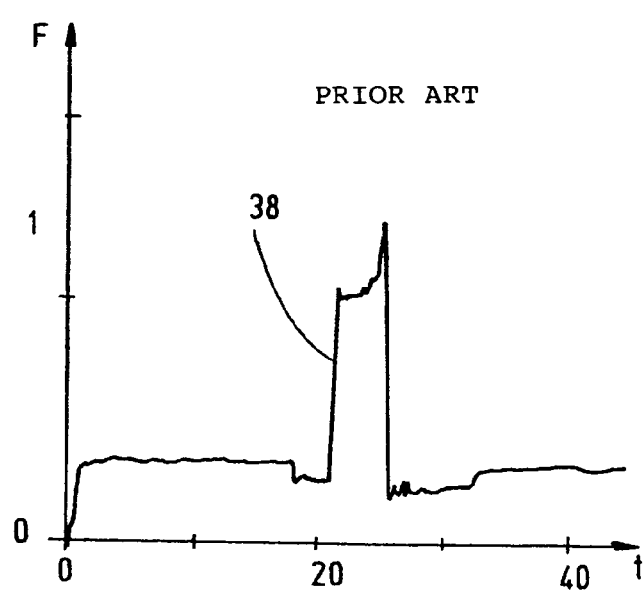
FIG. 4 shows a force diagram for the tape being pulled through a conventional seal according to the prior art.

Whereas peak forces are avoided by the oblique positioning of the test fields 16 or seal 24 according to the invention, FIG. 4 shows a force diagram for tape passage with an arrangement according to the prior art in which the sealing edge 30 and leading edge 32 are parallel to one another. In this case there is a sudden increase in force 38 when a test field passes through the seal which overall leads to an uneven tape movement and requires a strong tape drive.

Having described the invention in detail and by reference to specific embodiments thereof, it will be apparent that modification and variations are possible without departing from the scope of the invention defined in the appended claims. More specifically, although some aspects of the present invention are identified herein, it is contemplated that the present invention is not necessarily limed to these aspects of the invention.

What is claimed is:

1. Device for analyzing a body fluid, the device comprising a test tape having a carrier tape and test fields, the test fields having test chemistry for the detection of an analyte in the body fluid, the test fields being distributed along the carrier tape and raised above the carrier tape and a container for the test tape, the container having a seal for passage of the test tape, wherein the test fields have a leading edge which runs against a sealing edge of the seal when the test field passes through the seal, wherein the leading edge of the test fields at least in parts are angled relative to a transverse direction of the tape;

wherein each of the test fields has a thickness by which the test fields rise from the carrier tape; and wherein the seal has a flexible sealing area that is flexible to compensate for the thickness of the test fields by flexing to maintain a seal with the carrier tape, wherein the flexible sealing area contacts the carrier tape on a side of the carrier tape having the test fields, wherein the flexible sealing area rides up the test fields as the test fields pass through the seal to maintain the seal with the carrier tape.

2. Device according to claim 1 wherein the test fields have a tip delimited by the leading edge.

3. Device according to claim 1 wherein the test tape has a width and a longitudinal length, the leading edge of the test fields is diagonal to a longitudinal direction of the test tape at an angle that differs from 90° over the width.

4. Device according to claim 1 wherein the test tape has a width and a longitudinal length, the sealing edge interacting with the test tape extends diagonally to a longitudinal direction of the tape over the test tape width.

5. Device according to claim 1 wherein the sealing edge and the leading edge enclose an angle of at least 5°.

6. Device according claim 1 wherein the seal is profiled.

7. Device according to claim 6 wherein the seal is rounded in a vertical direction of the test tape.

8. Device according to claim 1 wherein the sealing edge at least in parts are angled or curved relative to the transverse direction of the tape.

9. Device according to claim 1 wherein the container is formed by a cassette where the seal seals a storage chamber of the cassette for the test tape.

10. Device according to claim 1 wherein the seal has a flexible sealing area and is formed to be pressed against a broad side of the carrier tape that carries the test fields.

11. Device according to claim 1 wherein the test fields are applied to the test tape as prefabricated flat material components.

12. Device according to claim 11 wherein the test fields are glued onto the carrier tape.

13. Device for analyzing a body fluid, the device comprising a test tape having a carrier tape and test fields, the test fields having test chemistry for the detection of an analyte in the body fluid, the test fields being distributed along the carrier tape and raised above the carrier tape;

a container for the test tape, the container having a seal for passage of the test tape, wherein the test fields have a leading edge which runs against a sealing edge of the seal when the test field passes through the seal, wherein the sealing edge at least in parts are angled or curved relative to a transverse direction of the tape;

wherein each of the test fields has a thickness by which the test fields rise from the carrier tape; and wherein the seal has a flexible sealing area that is flexible to compensate for the thickness of the test fields by flexing to maintain a seal with the carrier tape, wherein the flexible sealing area contacts the carrier tape on a side of the carrier tape having the test fields, wherein the flexible sealing area rides up the test fields as the test fields pass through the seal to maintain the seal with the carrier tape.

14. Device according to claim 13 wherein the test tape has a width and a longitudinal length, the sealing edge interacting with the test tape extends diagonally to a longitudinal direction of the tape over the test tape width.

15. Device according to claim 13 wherein the sealing edge and the leading edge enclose an angle of at least 5°.

16. Device according claim 13 wherein the seal is profiled.

17. Device according to claim 16 wherein the seal is rounded in a vertical direction of the test tape.

18. A device for analyzing a body fluid, the device comprising:
a test tape cassette including
a housing defining a storage space,
a carrier tape stored inside the storage space of the housing,
a seal having a sealing edge that presses against the carrier tape to seal the storage space,
the carrier tape having a plurality of test fields spaced apart along a longitudinal direction of the carrier tape, the test fields having test chemistry for detecting analyte in the body fluid, the test fields being raised from the carrier tape, the test fields each having a leading edge that runs against the sealing edge of the seal when the carrier tape is pulled through the seal, wherein the leading edges of the test fields and the sealing edge of the seal contact one another at an oblique angle relative to one another so that pulling force on the carrier tape is gradual when the test fields pass through the seal, wherein each of the test fields has a thickness by which the test fields rise from the carrier tape, and wherein the seal has a flexible sealing area that is flexible to compensate for the thickness of the test fields by flexing to maintain a seal with the carrier tape, wherein the flexible sealing area contacts the carrier tape on a side of the carrier tape having the test fields, wherein the flexible sealing area rides up the test fields as the test fields pass through the seal to maintain the seal with the carrier tape.

19. The device according to claim 18, wherein the leading edges of the test fields extend diagonally relative to the longitudinal direction of the carrier tape for avoiding abrupt edge contact between the sealing edge of the seal and the leading edges of the test fields.

20. The device according to claim 18, wherein the sealing edge of the seal extends diagonally relative to the longitudinal direction of the carrier tape to reduce peak pulling force when the test fields are pulled through the seal.

21. The device according to claim 18, wherein the seal has a flexible sealing area that is flexible to create a dragging surface seal when pressed against the carrier tape.

* * * * *